United States Patent [19]

Lea et al.

[11] Patent Number: 5,428,451
[45] Date of Patent: Jun. 27, 1995

[54] PROCESS AND APPARATUS FOR COUNTING PARTICLES

[75] Inventors: Tor E. Lea, Oslo; Bjørn K. Pedersen, Haslum; Harald K. Naess, Oslo, all of Norway

[73] Assignee: Diatec Instruments A/S, Oslo, Norway

[21] Appl. No.: 852,185
[22] PCT Filed: Dec. 6, 1990
[86] PCT No.: PCT/EP90/02121
  § 371 Date: Jun. 18, 1992
  § 102(e) Date: Jun. 18, 1992
[87] PCT Pub. No.: WO91/09297
  PCT Pub. Date: Jun. 27, 1991

[30] Foreign Application Priority Data
  Dec. 7, 1989 [GB] United Kingdom ........... 8927742

[51] Int. Cl.⁶ .................. G01N 15/14; G01N 21/64
[52] U.S. Cl. .......................... 356/417; 250/458.1; 377/10
[58] Field of Search .............. 377/10, 11; 356/417; 250/458.1, 459.1, 461.1, 461.2

[56] References Cited
U.S. PATENT DOCUMENTS

| | | | |
|---|---|---|---|
| 4,075,462 | 2/1978 | Rowe | 377/10 |
| 4,295,199 | 10/1981 | Curry et al. | 377/10 |
| 4,550,417 | 10/1985 | Nunogaki et al. | 377/10 |
| 4,576,477 | 3/1986 | Corbet et al. | 356/39 |
| 5,147,806 | 9/1992 | Kamin et al. | 436/149 |

FOREIGN PATENT DOCUMENTS

| | | |
|---|---|---|
| 0195420 | 1/1988 | European Pat. Off. |
| 61-51569 | 3/1986 | Japan |
| WO91/09308 | 6/1991 | WIPO |

OTHER PUBLICATIONS

Patent Abstracts of Japan, vol. 10, No. 212, Jul. 24, 1986, JP 61-51569.

*Primary Examiner*—F. L. Evans
*Attorney, Agent, or Firm*—Foley & Lardner

[57] ABSTRACT

Particles in a fluid are counted by passing the fluid through an optical cell and an image of said particles is projected onto an array of charge coupled devices such that the area of the image of each particle at the said array is approximately the same as the area of at least a single charge coupled device, and signals from the individual charge coupled devices are processed to provide information concerning at least the number of said particles passing through the optical cell. A particle counter disclosed comprising an optical cell (1) through which is passed a fluid containing particles to be counted, means (2) for illuminating the particles in the optical cell and optical means (3) for providing an image of the particles on an array of charge coupled devices (5) such that the area of the image of each particle at the said array is approximately the same as the area of at least a single charge coupled device. The particles may fluoresce and a transmittance filter (4) may be provided.

10 Claims, 1 Drawing Sheet

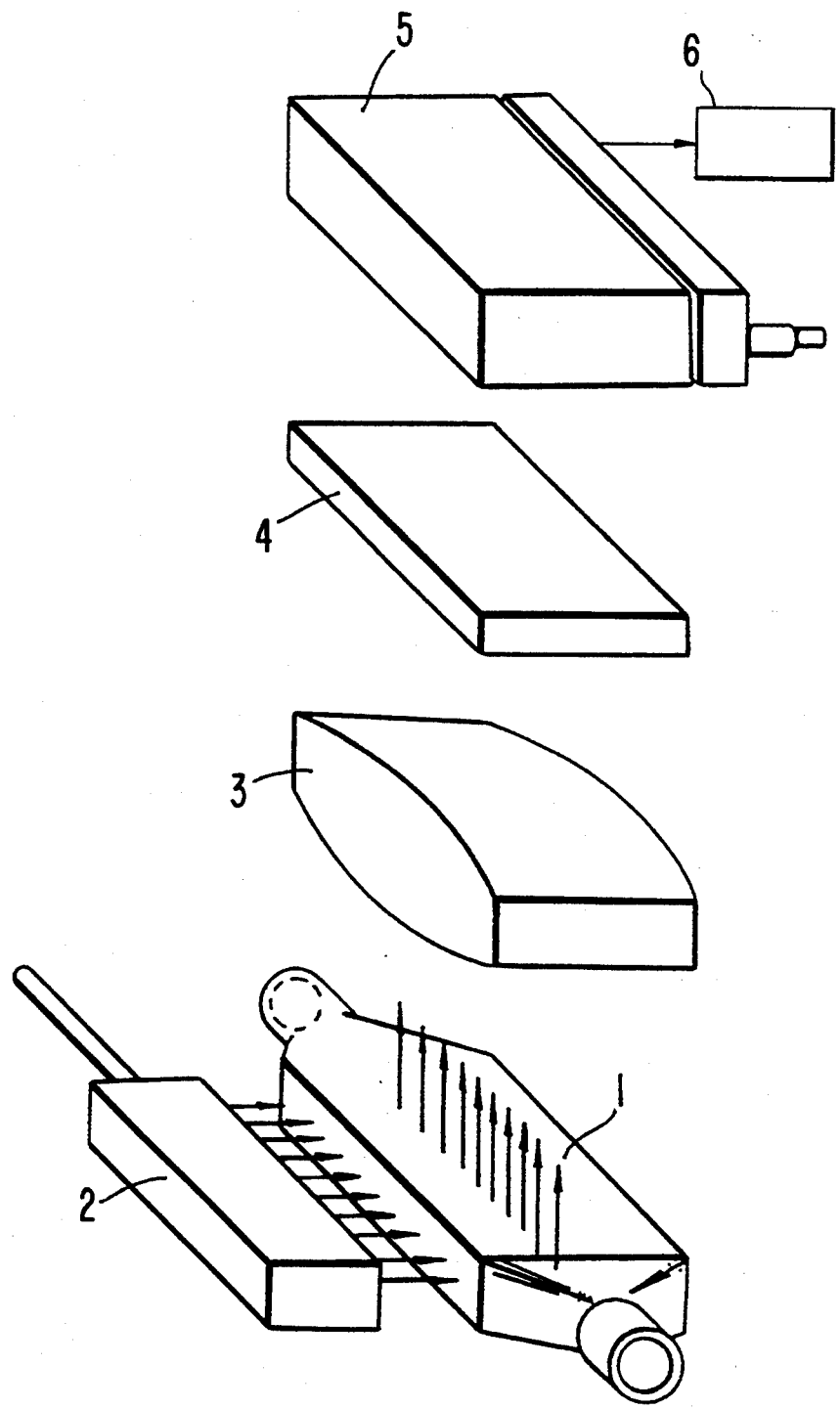

PROCESS AND APPARATUS FOR COUNTING PARTICLES

This invention concerns a method and apparatus for counting particles.

Existing particle counters, for example, for counting microbial cells, are cumbersome and expensive devices commonly employing a significant power source either to maintain a high voltage field, as in the Coulter system, or laser illumination as in the conventional flow cytometer. It would be convenient in many cases count particles accurately in the field using a system readily capable of transportation and using a portable power source, e.g., batteries.

U.S. Pat. No. 4,075,462 describes a particle analyser system in which images of particles are focused onto an array of light sensitive electronic elements. Only photodiodes are specifically described. The particles pass through a light path directly from a light source to the light sensitive array, thus providing a shadow image of the particles, while bubbles, which should not be counted, show up as having an apparent central aperture. Such a system is less well adapted to counting cells, which are normally relatively transparent, than more solid particles and does not lend itself to counting differentially stained particles.

Patent Abstracts of Japan, Vol 10, No. 212 (P-480) (2268), Jul. 24, 1986 and JP-A-6151569 describe a cell identifying device in which cells pass through a rectangular light beam and the intensity of forward and backward scattered light is measured as well as the spectral distribution of fluorescence. The scattered light is passed to a one-dimensional array of photosensors and is repeatedly scanned, the information being processed by a computer to enable the required cell identification to be effected. Forward and backward scatter of incident light can only give information on the granularity or surface structure of the cells while the fluorescence spectrum also gives information concerning the natural fluorescent chromophores on the cell surface. There is no suggestion that images of the cells are produced. The light scattered from the cells is not focused or collimated and the photosensor array is only one-dimensional, which does not lend itself to cell counting, where it is necessary to distinguish clearly the boundaries between the individual cells. Further, there is no attempt to prevent the scattered incident light from reaching the photosensors, for example by interpolation of a transmittance filter and, indeed, measurement of the scattered incident light is an essential part of the system.

BRIEF DESCRIPTION OF THE FIGURE

The Figure is an exploded perspective view of the components constituting the present invention.

DETAILED DESCRIPTION OF A PREFERRED EMBODIMENT OF THE INVENTION

The present invention is based in part on the concept of using an array of charge coupled devices (CCDs) as the counting device to count fluorescent particles. It is proposed, to project an image of the fluorescent particles onto the CCD array such that the area of the image of an individual particle is approximately the same as the area of at least one CCD. The particles are irradiated from the side and the incident irradiation is filtered out from the light falling on the CCD array, using one or more transmittance filters. However, in conventional, commercially available CCD arrays (chips) the area of each CCD, although very small, is larger than that of a typical microbial or other cell or cell nucleus or of many other particles, such as dust particles, which it may be require to count. Thus a preferred form the invention includes projecting a magnified image of the particle. This avoids the problem that a single CCD will provide a signal deriving from several particles simultaneously, thus preventing the possibility of counting individual particles.

The term CCD array as used herein refers to an array of photosensitive CCDs which may for example, be of the frame-field or interline transfer type and may produce the required signals by current or voltage sensing. Such arrays are normally provided as integral CCD chips for use, for example, in solid state cameras and one commercially available CCD chip is that available from Phillips N.V.

According to the present invention, therefore, we provide a method of counting particles in which a fluid containing said particles is passed through an optical cell and an image of said particles is projected onto an array of charge coupled devices such that the area of the image of each particle at the said array is approximately the same as the area of at least a single charge coupled device, and signals from the individual charge coupled devices are processed to provide information concerning at least the number of said particles passing through the optical cell characterised in that said particles are illuminated approximately perpendicular to a light path from the optical cell to the array of charged coupled devices to cause said particles to fluoresce and at least one transmittance filter is disposed between the optical cell and the array of charged coupled devices.

According to a further feature of the invention we provides a particle counter comprising an optical cell (1) through which is passed a fluid containing particles to be counted, means (2) for illuminating the particles in the optical cell and optical means (3) for providing in operation an image of the particles in an array of charge coupled devices (5) such that the area of the image of each particle at the said array is approximately the same as the area of a least a single charge coupled device characterised in that the means (2) for illuminating the particles provides radiation approximately perpendicular to a light path from the optical cell to the array of charged coupled devices (5) and is adapted to cause the particles to fluoresce and at least one transmittance filter (4) is disposed between the optical cell and the array of charged coupled devices.

The diameter of each CCD in the array will commonly be in the range 5-10 microns e.g. 6-7 microns. This is of the same order as many particles which may advantageously be counted, for example cell nuclei.

The image projected on to the CCD array is preferably magnified. The magnification of the image of the particles may be in the range 2 to 15, preferably 5 to 10. If necessary, additional lenses may be moved in and out of the optical path or may be moved therein to change the magnification.

It is possible to derive the number of particles in the fluid using merely a strip-like array of CCDs having only 2 or 3 CCDs in the direction of fluid flow but it is much better to use a larger array of CCDs to provide the possibility of as many as 10 'pictures' of each particle as its image moves across the CCD array e.g. a minimum of 30 rows of CCDs; this permits greater statistical analysis of the information and much greater accuracy of counting, as well as the possibility of providing information on particle size distribution. In general, it is preferred to use a conventional CCD chip, comprising of the order of 412×419 CCDs.

The signals from the CCD array can be processed by a computer, which may be a relatively unsophisticated personal computer, using appropriate software.

The software is designed to interrogate the CCDs as small groups or clusters, for example 3×3 CCDs. In any such group of 3×3 CCDs, it will be appreciated that if the size of the particle image is at least of the same order as one CCD, a number of CCDs will be at least partially covered by the image of the particle and provide a signal while the remainder will indicate the absence of the image. This enables the coordinates and boundaries of the image on the CCD array to be established. The particle concentration or the dimensions of the particle stream will be adjusted to ensure adequate spacing of the particles. The information provided by the CCDs can give an indication of particle size as well as position. As the images of the particles traverse the CCD array, the information concerning each particle can be checked several times. Sampling will generally be of the order of 50 times per second. If the particle stream is found to be moving too fast for accurate counting, the speed may be controlled, for example by feedback of information from the CCDs.

It may be desirable to count only particles emitting light of a particular colour and it is then desirable for the transmittance filter between the optical cell and the CCD array to transmit only that colour. Thus, in counting cells or cell-nuclei stained with a fluorescent dye, it may be desirable to use a filter transmitting only light of the required wavelength. This avoids counting any unstained particles as well as cutting out any of the radiation used to illuminate the particles in such a fluorescent system.

It is also possible to count more than one population of cells simultaneously if these are sufficiently differentiated either by size and/or colour. In the case of colour differentiation, it is necessary to use more than one transmittance filter which may, for example, be mounted on a rotating device introducing the filters successively into the light path, possibly separated by light obstructing sections so that light of different colours will be intermittently projected onto the CCD array. The rotation of the above device can readily be synchronised with the signal processing system to distinguish the images produced by the differently coloured particles.

The optical cell is illuminated by radiation incident approximately perpendicular to the light path from the cell to the CCD array. This maximises the contrast between the particle image and the background. It is particularly preferred to use devices according to the invention to count cells stained with a fluorescent dye. In general, the side-illumination will be a source of ultra-violet light.

Data processed by a computer connected to the chamber may be displayed, for example on a LCD display (particularly where battery power only is desirable) and can give not only particle numbers but a histogram or other representation of size and/or colour distribution. A printer, e.g. a thermal printer, may be attached to provide a hard copy print-out of the information.

The optical cell may be of design conventional for cell counting. It is preferred that the flow path is very thin so that only a single layer of particles is counted and overlap is minimised. The width of the cell will be such that the image of the cells on the CCD array falls within the dimensions of the array. Alternatively, the image falling on the CCD array can be derived solely from a known restricted area of the cell comprising a fixed fraction of the width of the cell, so that only a known proportion of the particles is counted. Typically, for biological cell counting, the dimensions of the optical cell may be: thickness 0.1 mm ×width 4 mm ×length 4 mm, thickness being the dimension perpendicular to the optical path of the imaging system.

However, use of a high quality, short focal length optical system for projecting an image of the particles onto the CCD array enables a thin slice of the fluid to be visualised selectively. The volume of the slice can be determined and will effectively comprise the volume of fluid subjected to particle counting. This provides a simple alternative to the use of laser light in conventional cytometers to provide and accurate thin layer of illumination. Lasers require a power supply which cannot be provided by batteries even on an intermittent basis whereas, as indicated above, it is an advantage of the devices of the present invention that they can be powered solely by batteries and may thus be used when an electrical main or power source is unavailable.

The system and device according to the invention are particularly useful in conjunction with the magnetic particle separation device according to our co-pending International Application No. PCT/EP90/02122 claiming priority from GB 8927744.6, filed Dec. 7, 1989. This enables superparamagnetic particles to be attached to analytes including biological cells and readily separated from reagents and unwanted contaminants (such as cells other than those of interest) before being passed to the particle counting device. This enables cells in a diverse population, e.g. a blood sample, readily to be counted, and provides a valuable tool for the diagnosis of diseases. Generally, such a separation device may comprise a chamber provided with opposed electromagnets which can be energised in turn. Energisation of the first magnet causes magnetic particles within tile chamber to aggregate onto the chamber wall near that magnet. After removal of supernatant and introduction of a further fluid, the particles may be re-dispersed, by energising the other magnet and causing the particles to move across the fluid to the other wall. This procedure can be repeated to complete that particular process stage and, with the particles aggregated on the wall, the fluid may be removed. Such a chamber may be provided with a fluid supply system whereby the sample and successive wash and reagent fluids may be introduced into the chamber via appropriate tubing by pressure transfer. This can readily be automated using electrically controlled pinch valves to permit transfer of an appropriate volume of each individual solution.

The magnetic particles are typically attached to selected cells via specific monoclonal antibodies bound to the surface of the magnetic particles. After processing, it may be more convenient to lyse the cells and count only the nuclei which have previously been stained by a fluorescent dye. However, whole cells may be passed to the particle counter with magnetic particles attached since these are very much smaller than the cells and will not interfere with counting.

Such magnetic particles may be used to bind to analytes other than cells and then, for example in a sandwich assay, labelled with an optical label e.g. fluorescent dye. The magnetic particles, after removal of unreacted label, may then be passed to the counter together with unreacted magnetic particles, which can be distinguished by their lack of attached fluorescent label.

The invention will now be described by way of illustration only with reference to FIG. 1 of the accompanying drawings which shows schematically a particle counting device according to the invention.

In the device shown in FIG. 1, an optical cell 1 (0.1 mm ×4 mm ×4 mm) is illuminated on one side by an ultraviolet light source 2. A magnifying optical system, schematically represented by the lens 3, is positioned in a light path perpendicular to the incident UV light from the source 2 and a transmittance filter 4 is also positioned in the light path. A CCD array 5, typically a CCD chip (9×6 mm) is provided at the end of the light path and receives a magnified image of particles in the counter focused onto the surface of the CCDs. By appropriate focusing, light can be selected from a layer or slice of the interior of the optical cell 1, the volume of this slice being known or calibrated so that the number of particles per unit volume of the fluid may be calculated.

The cell 1 typically is made from optical quality glass although optical plastics may be used. The shape of the cell is designed to fit the optical lens system 3 and the CCD chip 5. The lens system has a magnification ratio that will make a normal particle (e.g. a nucleus) cover up to 3×3=9 CCDs in the CCD chip 5. By choosing this ratio, the analyzer facilitates measurements of both smaller and larger particles than normal. The CCD chip is chosen on the basis of its CCD density, sensitivity and reaction time.

Since the fluorescent dye, e.g. acridine orange, has a definite wavelength for its emission, the filter 4 is placed between the lens system 3 and the CCD chip 5 to filter out light of other wavelengths.

The CCD chip gives continuous information regarding what is happening in its viewing field. This information is transmitted to the processing unit 6 in the analyzer.

The analyzer includes a computer (not shown) which handles all communication with the operator and all data analysis. Communication with the operator is via a conventional touch sensitive panel, such as a keyboard, and an LCD screen (neither of which are shown). At the beginning of the analysis the computer will tell the operator to check certain functions and how to insert the sample. The processor will control the valve function and monitor the pressure in the fluid system. The energisation of the magnetic fields is controlled and the data from the CCD chip 5 is collected.

The information from the CCD chip may, for example, be sampled as 10 "frame freeze pictures", because the information from the CCD chip will be real time information from a moving fluid. The information from the 10 pictures will be processed by appropriate imaging software capable of identifying the number of illuminated objects and the size distribution.

The data obtained from the 10 pictures is treated statistically and the results for the test are calculated.

The results of the analysis are presented on the LCD screen in terms of the number of cells and a histogram of the size distribution although other presentations will be apparent to the skilled person. The latter will give the operator a chance to see if the sample contained so many abnormal cells that further study is necessary.

A printer, e.g. a thermal printer, may be provided to print out a hard copy of the test results.

We claim:

1. A method of counting particles, including the steps of:
   (a) passing a fluid containing said particles through an optical cell;
   (b) projecting images of said particles onto an array of charge coupled devices, such that the area of the image of each particle projected on the array is at least approximately the same in area as that of a single charge coupled device; and
   (c) processing signals from individual charge coupled devices to provide information indicative of the number of particles passing through the optical cell; whereby,
   the particles as they pass through the optical cell are illuminated from an illumination source in a direction approximately perpendicular to a light path from the optical cell to the array of charge coupled devices, the illumination causing the particles to fluoresce.

2. The method of counting particles as claimed in claim 1, in which at least one transmittance filter is disposed in the light path.

3. The method of counting particles as claimed in claim 1, wherein the images of said particles are projected onto the charge coupled devices by a magnifying lens means.

4. The method of counting particles as claimed in claim 1, in which the array of charge coupled devices are interrogated in clusters, the charge coupled devices in each cluster being interrogated approximately simultaneously.

5. The method of counting particles as claimed in claim 1, in which the projected image of each particle is such that projected images of different particles do not fall on a same one of said charge coupled devices.

6. A particle counter comprising:
   an optical cell through which passes a fluid containing particles to be counted;
   means for illuminating the particles in the optical cell; and
   optical means for projecting onto an array of charge coupled devices images of the particles passing through the optical cell, the area of the image of each particle projected onto the array being at least approximately the same in area as that of a single charge coupled device; wherein,
   the illuminating means provides radiation approximately perpendicular to a light path from the optical cell to the array of charge coupled devices, the radiation causing the particles to fluoresce.

7. The particle counter as claimed in claim 6, further including at least one transmittance filter is disposed in the light path.

8. The particle counter as claimed in claim 6, further including an optical means in the light path for providing a magnified image of the particles on the array of charge control devices.

9. The particle counter as claimed in claim 6, further including means for processing signals from the individual charge coupled devices, to provide information concerning the number of particles passing through the optical cell.

10. The particle counter as claimed in claim 6, in which the projected image of each particle is such that projected images of different particles do not fall on a same one of said charge coupled devices.

* * * * *